(12) United States Patent
Takahashi et al.

(10) Patent No.: US 7,968,049 B2
(45) Date of Patent: Jun. 28, 2011

(54) COMPONENT SEPARATING DEVICE AND METHOD OF SEPARATING COMPONENT

(75) Inventors: Makoto Takahashi, Osaka (JP); Masaya Nakatani, Hyogo (JP)

(73) Assignee: Panasonic Corporation, Osaka (JP)

( * ) Notice: Subject to any disclaimer, the term of this patent is extended or adjusted under 35 U.S.C. 154(b) by 915 days.

(21) Appl. No.: 11/721,734

(22) PCT Filed: Apr. 24, 2006

(86) PCT No.: PCT/JP2006/308542
§ 371 (c)(1),
(2), (4) Date: Jun. 14, 2007

(87) PCT Pub. No.: WO2006/115241
PCT Pub. Date: Nov. 2, 2006

(65) Prior Publication Data
US 2009/0250406 A1 Oct. 8, 2009

(30) Foreign Application Priority Data
Apr. 25, 2005 (JP) .................................. 2005-126040

(51) Int. Cl.
*B01D 43/00* (2006.01)
*B01J 19/00* (2006.01)
*C02F 1/36* (2006.01)
(52) U.S. Cl. ........ 422/20; 422/22; 210/748.01; 210/523
(58) Field of Classification Search .. 210/748.01–748.1, 210/201, 523; 422/22, 24, 99, 101, 20; 204/222, 204/223
See application file for complete search history.

(56) References Cited

U.S. PATENT DOCUMENTS
5,902,489 A * 5/1999 Yasuda et al. .............. 73/863.21

FOREIGN PATENT DOCUMENTS
| JP | 11-197491 | 7/1999 |
| JP | 2001-050940 | 2/2001 |
| JP | 2001-525722 | 12/2001 |
| JP | 2004-024959 | 1/2004 |
| JP | 2004-097851 | 4/2004 |
| WO | WO 2004/033087 A1 | 4/2004 |

OTHER PUBLICATIONS

International Search Report for application No. PCT/JP2006/308542 dated Jun. 13, 2006.
Yong-Kyu Yoon, "Integrated Vertical Screen Microfilter System Using Inclined SU-8 Structures" MEMS2003, Kyoto, IEEE, pp. 227-230.

* cited by examiner

*Primary Examiner* — Nam X Nguyen
*Assistant Examiner* — Cameron J Allen
(74) *Attorney, Agent, or Firm* — RatnerPrestia

(57) ABSTRACT

A component separating device includes a substrate, a fluid channel provided at the substrate, an actuator and a groove provided at a surrounding of the actuator, the fluid channel contains a fluid including a liquid component and a solid component, and the actuator generates a standing wave at inside of the fluid channel. By such a constitution, a vibration loss is reduced by reflecting a vibration by the groove to be transmitted to a side of the fluid channel, the standing wave having a strong intensity is generated at inside of the fluid channel, and the small-sized highly accurate component separating device is provided.

15 Claims, 9 Drawing Sheets

COMPONENT SEPARATING DEVICE AND METHOD OF SEPARATING COMPONENT

This Application is a U.S. National Phase Application of PCT International Patent Application No. PCT/JP2006/308542, filed Apr. 24, 2006.

TECHNICAL FIELD

The present invention relates to a component separating device and a method of separating a component for separating a fluid mixed with a liquid component and a solid component, represented by blood, milky liquid or the like into respective components.

BACKGROUND ART

As a fluid mixed with a solid component and a liquid component, for example, river water, sea water, blood, milky liquid or the like is included. Solid components of sand, bacteria, blood cell, emulsion or the like included in the fluids are present at inside of the fluids in a state of precipitation, dispersion or the like. That is, the solid component is present as a solid without being dissolved in the liquid component.

An explanation will be given of a method, a device of separating the fluid mixed with the solid component and the liquid component into respective components of, for example, a blood cell/blood plasma separating device or the like as follows.

Normally, blood sampled for inspection is sampled in a whole blood state constituted by blood plasma which is a liquid component, a blood cell which is a solid component and other component. However, there is frequently a case in which a component necessary for inspecting blood is only a blood cell portion, or conversely, a blood plasma portion. For example, in order to inspect a blood sugar level in blood, blood sugar dissolved in a blood plasma component is measured. In order to inspect DNA, DNA is sampled from leukocyte cell which is a kind of blood cell.

Therefore, in order to inspect blood, prior to inspection, there is used a step of separating respective components present in blood. A method of separating a component of a background art is generally a method of putting sampled blood in a whole blood state into a test tube to be mounted to a centrifugal separator and applying a predetermined centrifugal force to thereby separate blood into a blood plasma component and a blood cell component.

In this way, the blood in the whole blood state at inside of the test tube is applied with the centrifugal force by the centrifugal separator. Thereby, respective components undergo centrifugal forces in accordance therewith to be separated into the respective components by differences in masses. Thereafter, by extracting a supernatant fluid, the blood plasma component is taken out. The blood cell component or the like is taken out from a precipitate. Thereafter, the respective components are inspected by being subjected to predetermined measurement in an inspecting step.

In separating the components by the centrifugal separator, in view of operation of the centrifugal separator, a constant amount or more of a fluid is needed and the separation is not suitable so much when a sample amount is small.

As a method of separating a sample of a small amount of a liquid, there is also a method of using a filter. The method is a method disclosed by Yong-Kyu Yoon and other, which utilizes a porous characteristic of the filter. For example, by filtering blood cell having a predetermined size or more, the blood plasma component is provided, conversely, blood cell is taken out. According to the method, a hole size, number or the like of the filter have an influence on a separating characteristic. Therefore, it is required to design an optimum filter by which component is to be separated. It is also required to accurately reproduce the hole size, number or the like of the filter. For example, a method of accurately reproducing hole size, number or the like of the filter is a method of providing a filter in a mesh-like shape by exposing a photosensitive resist three-dimensionally. The method is disclosed in, for example, Yong-Kyu Yoon "Integrated vertical screen microfilter system using inclined SU-8 structure." MEMS2003, Kyoto, PP. 227-230 issued by IEEE.

Also a device for carrying out manipulation of particles suspended in a fluid is utilized. The component separating method, for example, is disclosed in Japanese Translation of PCT Publication No. 2001-525722 (hereinafter, referred to as Patent Reference 1). A component separating apparatus disclosed in Patent Reference 1 includes a duct, an ultrasonic transducer, and a reflector. The duct is provided for making the fluid suspended with particles flow. The ultrasonic transducer is arranged on one side of the duct and the reflector is arranged on an opposed side of the duct. An acoustic standing wave vibration (hereinafter, referred to as standing wave) traversing the duct in a width direction is generated by the duct, the ultrasonic transducer and the reflector. By the standing wave, particles suspended in the fluid are agglomerated to constitute one or more of plane bands in parallel with a longitudinal axis of the duct. Thereby, particles, which are a solid component, and a liquid component are separated.

According to the constitution, the ultrasonic transducer is brought into direct contact with an inner portion of the duct and therefore, there is a case in which the ultrasonic transducer is contaminated by a fluid flowing at inside of the duct. Further, the ultrasonic transducer constitutes a part of the duct. Thereby, there is not a freedom of designing the ultrasonic transducer, further, it is difficult to accurately position the duct and the ultrasonic transducer.

SUMMARY OF THE INVENTION

The invention provides a component separating device and a method of separating a component capable of separating respective components highly accurately even by a small amount of a sample by generating an acoustic standing wave having a strong intensity.

A component separating device of the invention includes a substrate, a fluid channel provided at the substrate, an actuator and a groove provided at a surrounding of the actuator. The fluid channel contains a fluid including a liquid component and a solid component, and the actuator generates a standing wave at inside of the fluid channel. By this constitution, a vibration loss is reduced by reflecting a vibration by the groove to be transmitted to a side of the fluid channel, the standing wave having a strong intensity is generated at inside of the fluid channel to provide a small-sized and highly accurate component separating device.

A method of separating a component of the invention includes a fluid containing step, a standing wave generating step, a reflecting step and a separating step. At the fluid containing step, a fluid including a liquid component and a solid component is contained in a fluid channel provided at a substrate. At the standing wave generating step, a standing wave, which has a node at an inner portion of the fluid channel, is generated by generating a vibration by applying a high frequency voltage to a plurality of actuators provided to be opposed to the fluid channel to thereby. At the reflecting step, the vibration reflects at a groove provided at a surrounding of the actuator, the groove is provided at the surrounding excluding a side of the fluid channel, and at the separating step, at least either one of the liquid component and the solid component is separated from the fluid. By this constitution, a vibration loss is reduced by reflecting the vibration by the groove to be transmitted to the side of fluid channel, the standing wave having a strong intensity is generated at inside of the fluid channel to thereby provide the highly accurate method of separating the components.

Figure 1:
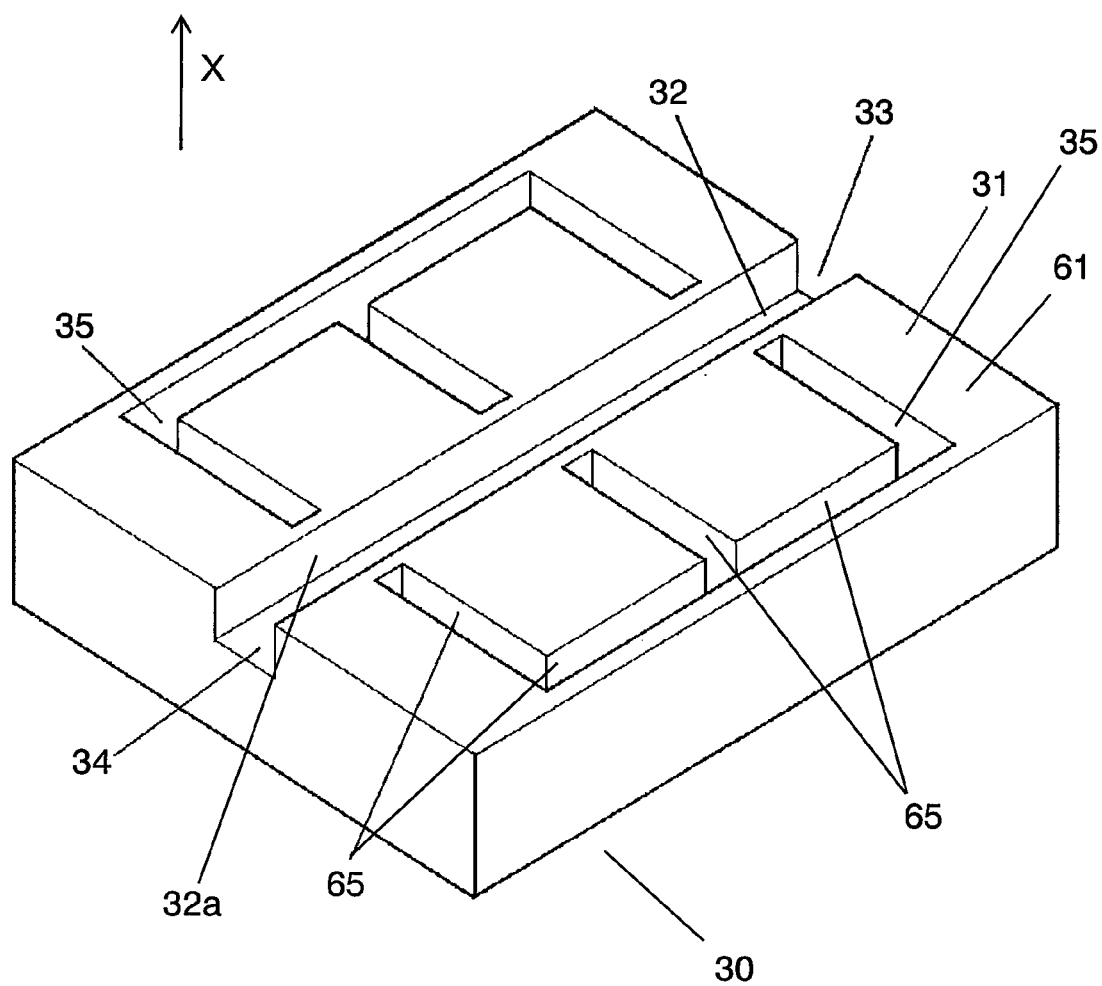
FIG. 1 is a perspective view showing a constitution of a component separating device according to Embodiment 1 of the invention.

REFERENCE MARKS IN THE DRAWINGS 31 substrate
32 fluid channel
33 flow inlet
34 flow outlet
35, 35a, 35b, 35c grooves
36, 36a, 36b, 36c, 36d lower electrodes
37, 37a, 37b, 37c, 37d piezoelectric members
38, 38a, 38b, 38c, 38d upper electrodes
39 actuator
39a first actuator
39b second actuator
39c third actuator
39d fourth actuator
40 fluid flow
41 solid component
41a first solid component
41b second solid component
42 liquid component flow
43, 43a, 43b solid component flows
44 first electrode layer
45 piezoelectric layer
46 second electrode layer
47 first resist mask
48 second resist mask
49 third resist mask
50 fourth resist mask
51 fifth resist mask
52, 52b, 52c first opening portions
53, 53b, 53c second opening portions
54 movable portion
61 upper face
62 lower face
63, 63a, 65 fluids
64 liquid component
65, 65a, 65b, 65c wall faces
70, 71 nodes

DETAILED DESCRIPTION OF PREFERRED EMBODIMENTS

First Exemplary Embodiment

An explanation will be given of a component separating device and a method of separating a component using the device according to Embodiment 1 of the invention in reference to the drawings as follows.

Figure 2:
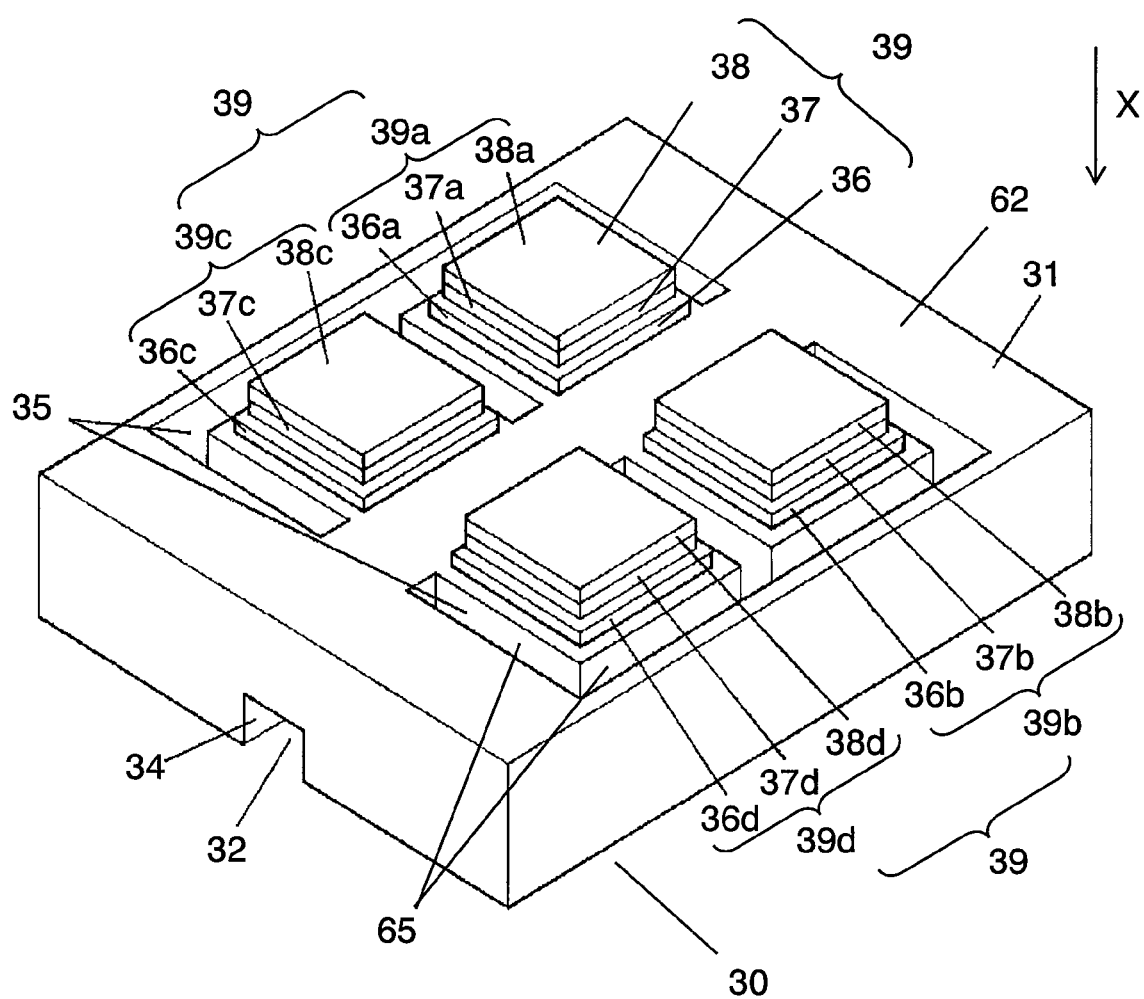
FIG. 2 is a perspective view of the component separating device shown in FIG. 1 viewed from a back face thereof.
Figure 3:
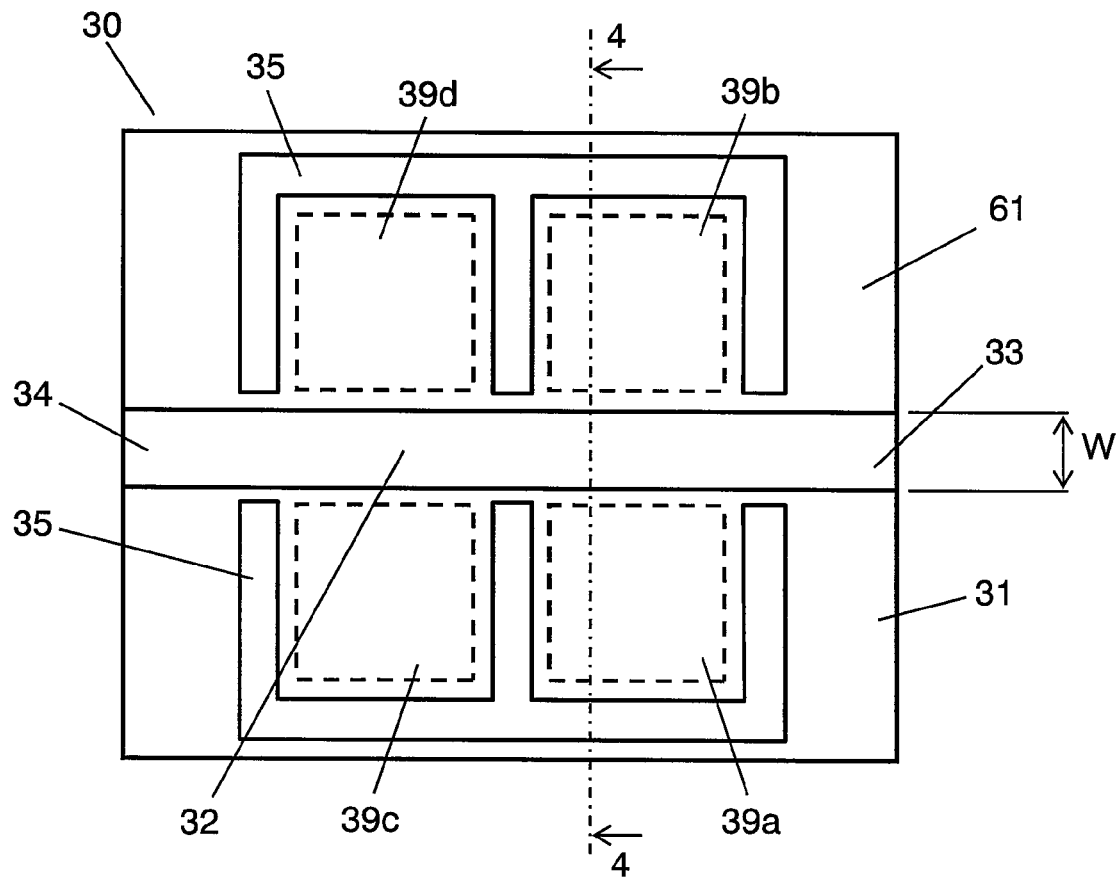
FIG. 3 is a plane view of the component separating device shown in FIG. 1.
Figure 4:
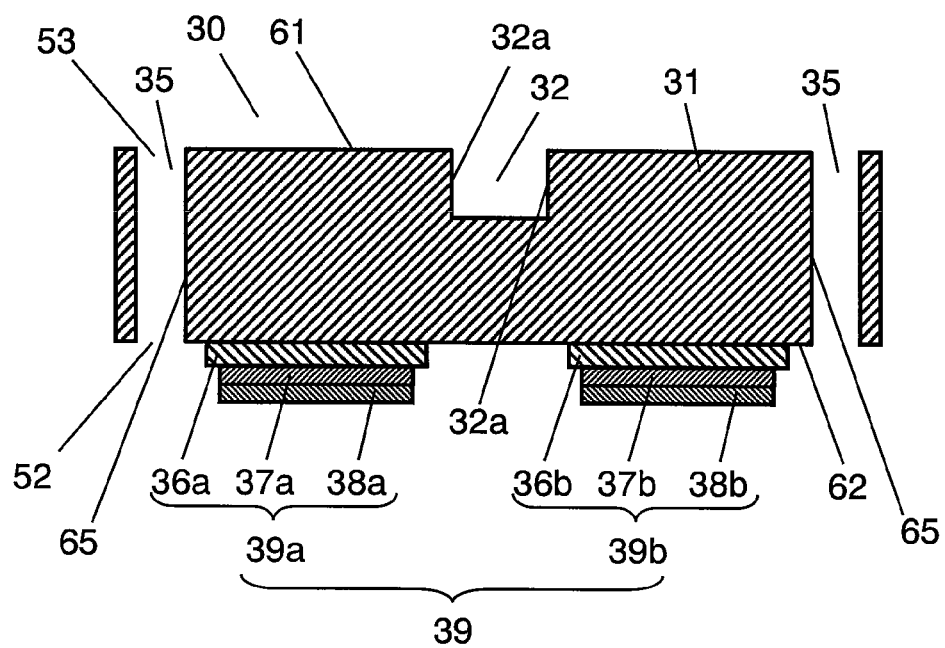
FIG. 4 is a sectional view taken along a line 4-4 of the component separating device shown in FIG. 3.

FIG. 1 is a perspective view showing a constitution of a component separating device according to Embodiment 1 of the invention. FIG. 2 is a perspective view of the component separating device shown in FIG. 1 viewed from a lower face side thereof. FIG. 3 is a plane view of the component separating device shown in FIG. 1. FIG. 4 is a sectional view taken along a line 4-4 of the component separating device shown in FIG. 3.

FIG. 5 through FIG. 8 are schematic views for explaining a method of separating a component using the component separating device shown in FIG. 1. FIG. 9 through FIG. 14 are sectional views for explaining a method of fabricating the component separating device shown in FIG. 1.

In FIG. 1 through FIG. 4, substrate 31 is formed by constituting a material thereof by silicon. Substrate 31 is formed with fluid channel 32 having a predetermined width and a predetermined depth. Fluid channel 32 is provided on a side of upper face 61 of substrate 31. Both ends of fluid channel 32 are provided with flow inlet 33 and flow outlet 34, respectively. Fluid 63 mixed with solid component 41 and liquid component 64 is made to flow from outside of fluid channel 32 to flow inlet 33 and is contained in fluid channel 32. Fluid 63 is made to flow out from flow outlet 34 to outside of fluid channel 32. During a time period in which fluid 63 made to flow into flow inlet 33 passes fluid channel 32 and is discharged from flow outlet 34, by operating component separating device 30, solid component 41 and liquid component 64, which are included in fluid 63, are respectively separated. By utilizing silicon for the material of substrate 31, component separating device 30 excellent in productivity is realized.

Actuators 39 are provided at a side of lower face 62 of substrate 31. Actuators 39 includes first actuator 39a (hereinafter, referred to as actuator 39a), second actuator 39b (hereinafter, referred to as actuator 39b), third actuator 39c (hereinafter, referred to as actuator 39c) and fourth actuator 39d (hereinafter, referred to as actuator 39d). Actuators 39a, 39b, 39c, 39d are provided respectively in parallel with each other along both sides of fluid channel 32 to be opposed to each other by way of fluid channel 32. A vibration is generated by driving actuators 39a, 39b, 39c, 39d. The generated vibration is transmitted by substrate 31 and a standing wave is generated at inside of fluid channel 32.

Fluid channel 32 and actuators 39a, 39b, 39c, 39d are constituted to set those face to the same axial direction (X axis direction of drawing) of substrate 31. Thereby, component separating device 30 further excellent in productivity is realized.

Component separating device 30 including four of actuators 39a, 39b, 39c, 39d will be explained as follows. However, the component separating device and the method of separating the component can be realized by providing at least one of actuators 39. Further, by providing a plurality of pieces of actuators 39, operation and effect of actuators 39 are achieved and small-sized component separating device 30 having a high separating function is realized.

Actuators 39a, 39b, 39c, 39d are respectively provided at lower face 62. Lower face 62 is a face at a side opposed to upper face 61 of substrate 31 and fluid channel 32 is provided at upper face 61. Thereby, positions of arranging actuators 39a, 39b, 39c, 39d and fluid channel 32 are not interfered with each other and therefore, actuators can freely be arranged. Thereby, generation of the standing wave at inside of fluid channel 32 is easily achieved. Fluid channel 32 is easily sealed by a glass substrate (not illustrated) or the like. Thereby, components are separated while confirming a situation of separating the components by eye observation.

Actuators 39 are constituted by lower electrode 36, piezoelectric member 37 and upper electrode 38 successively from the one brought into contact with substrate 31. Respective actuators 39a, 39b, 39c, 39d include respective lower electrodes 36a, 36b, 36c, 36d, respective piezoelectric members 37a, 37b, 37c, 37d, respective upper electrodes 38a, 38b, 38c, 38d. A material for constituting lower electrodes 36a, 36b, 36c, 36d includes at least either one of titanium and platinum. A material for constituting piezoelectric members 37a, 37b, 37c, 37d includes lead zirconate titanate. A material for constituting upper electrodes 38a, 38b, 38c, 38d includes at least either one of titanium and gold.

Actuators 39a, 39b, 39c, 39d having such a constitution generate a large displacement even when supplied power is constituted by a low voltage. Thereby, the vibration is generated efficiently. Actuators 39a, 39b, 39c, 39d include a laminated layer structure excellent in an adhering force and therefore, even when the vibration having the large displacement is continuously generated, excellent durability is realized in reliability. A highly accurate pattern can be formed by a material for constituting actuators 39a, 39b, 39c, 39d and therefore, actuators 39a, 39b, 39c, 39d are arranged at positions which are highly accurate relative to fluid channel 32. Therefore, actuators 39a, 39b, 39c, 39d realize to generate the standing wave further efficiently. As a result, small-sized, high-functioned component separating device 30 is easily realized.

As shown by FIG. 1 and FIG. 2, by providing respective pairs of actuators 39 at both sides of fluid channel 32, the standing wave is efficiently generated at inside of fluid channel 32. For example, there is constructed a constitution of arranging pairs of actuators 39 on both sides of fluid channel 32 by a combination of actuator 39a and actuator 39b, or a combination of actuator 39c and actuator 39d. By providing respective pairs of actuators 39 in a direction in parallel with fluid channel 32, standing waves having different frequencies can also be generated at inside of fluid channel 32. For example, there is constructed a constitution of arranging pairs of actuators 39 in the direction in parallel with fluid channel 32 by a combination of actuator 39a and actuator 39c, or a combination of actuator 39b and actuator 39d. When the plurality of actuators 39a, 39b, 39c, 39d are efficiently installed, by interactive operation of the plurality of actuators 39a, 39b, 39c, 39d, functions of actuators 39a, 39b, 39c, 39d are sufficiently achieved.

Grooves 35 are provided at portions of surroundings of actuators 39a, 39b, 39c, 39d which are not formed with fluid channel 32. As shown by FIG. 4, groove 35 is formed in a shape of a through hole completely penetrating from upper face 61 to lower face 62 of substrate 31. Thereby, an energy loss of the standing wave generated at fluid channel 32 is reduced. That is, by providing grooves 35, vibration generated by actuators 39a, 39b, 39c, 39d is restrained from being diverged to a surrounding of substrate 31. Thereby, the vibration is transmitted to fluid channel 32 efficiently and concentratedly. Therefrom, the standing wave having a stronger intensity is generated. Groove 35 is formed to partition actuators 39 contiguous to each other. Thereby, when actuators 39 contiguous to each other are driven by different frequencies, vibrations having different frequencies are prevented from being interfered with each other. Contiguous actuators 39 indicate, for example, a relationship between actuator 39a and actuator 39c, or actuator 39b and actuator 39d.

In this way, grooves 35 are formed at portions of surroundings of actuators 39a, 39b, 39c, 39d which are not formed with fluid channel 32. Thereby, vibrations generated by actuators 39a, 39b, 39c, 39d are reflected by wall face 65 of groove 35 and transmitted to a side of fluid channel 32. As a result, loss of vibrations, which are generated by actuators 39a, 39b, 39c, 39d, transmitted in directions other than a direction of fluid channel 32 is reduced. Therefrom, control of vibration transmitted to fluid channel 32 can easily be carried out. As a result, efficient component separating device 30 is realized.

Figure 5:
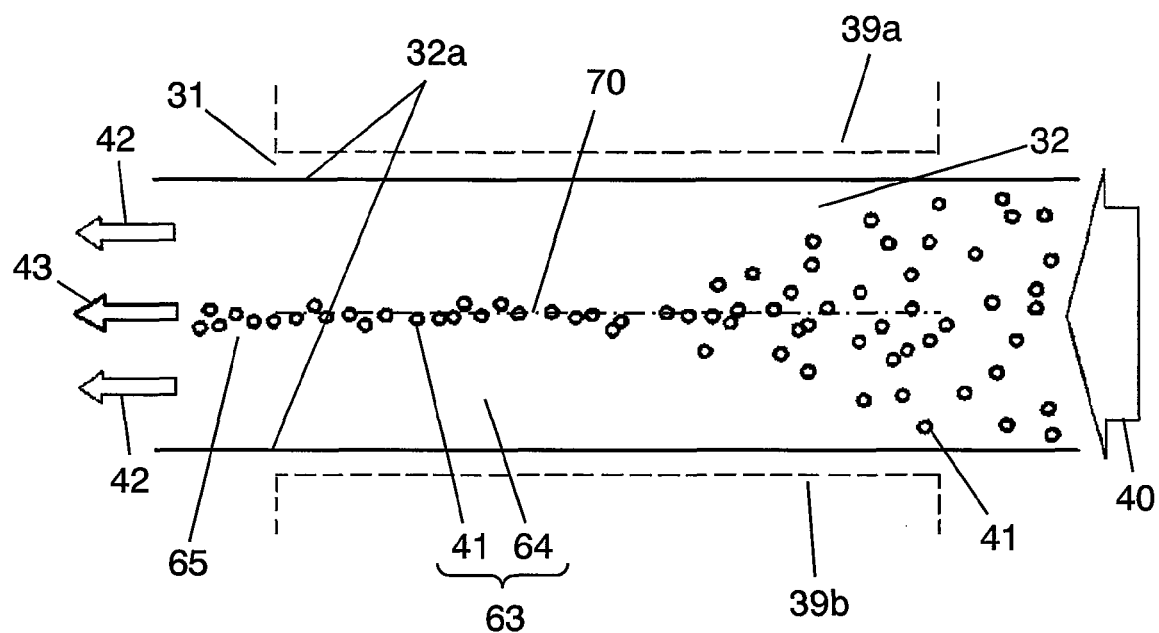
FIG. 5 is a schematic view for explaining a method of separating a component using the component separating device shown in FIG. 1.
Figure 6:
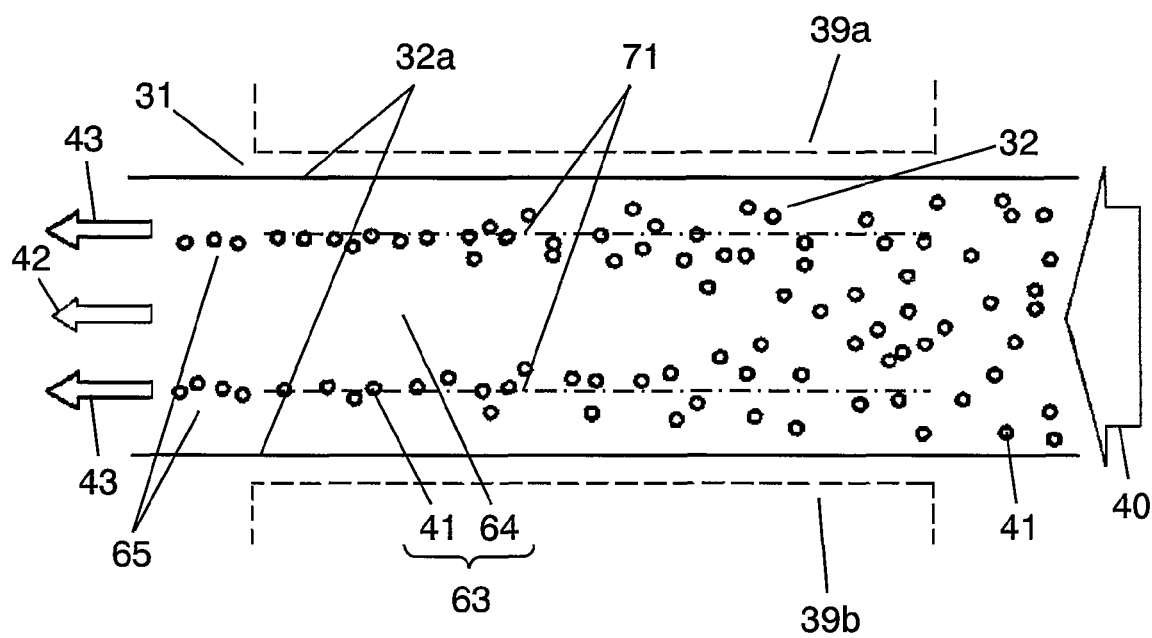
FIG. 6 is a schematic view for explaining the method of separating the component using the component separating device shown in FIG. 1.

Next, an explanation will be given of a method of separating respective components of a solid component and a liquid component from the fluid by using component separating device 30 in reference to FIG. 5 and FIG. 6. An explanation will be given of a method of separating respective solid components having different properties in reference to FIG. 7 and FIG. 8. FIG. 5 through FIG. 8 are respective plane views when component separating device 30 is observed from a side of upper face 61, particularly showing around fluid channel 32.

First, fluid 63 which is a mixture mixed with solid component 41 and liquid component 64 is made to flow from flow inlet 33. Fluid 63 is contained in fluid channel 32 and is made to flow out from flow outlet 34 after filling fluid channel 32. Fluid flow 40 indicates a direction in which fluid 63 flows. Normally, when component separating device 30 is not operated, fluid 63 is made to flow at inside of fluid channel 32 in a state of being irregularly mixed with solid component 41 and fluid component 64.

When component separating device 30 is operated, actuator 39a is applied with a high frequency voltage. A frequency of the high frequency voltage applied to actuator 39a is a frequency of a supersonic wave band constituting a width W of fluid channel 32 by ½ of a wavelength $\lambda$ ($\lambda=2\times W$). Actuator 39a generates a supersonic vibration when applied with the high frequency voltage. The supersonic vibration generated by actuator 39a is transmitted at substrate 31 and a standing wave is generated at inside of fluid channel 32. The standing wave includes one node 70 constituting an odd number in parallel with fluid channel 32. Fluid 63 contained at inside of fluid channel 32 flows at inside of fluid channel 32 such that solid component 41 is agglomerated to node 70. Thereby, as shown by FIG. 5, solid component flow 43 (hereinafter, referred to as flow 43) and liquid component flow 42 (hereinafter, referred to as flow 42) are produced. In flow 43, solid component 41 is agglomerated. In flow 42, solid component 41 is diluted.

Thereafter, after fluid 63 flows out from flow outlet 34, flow 42 and flow 43 are respectively branched. Thereby, liquid component 64 is taken out from a side of wall face 32a of fluid channel 32, and fluid 65 agglomerated with solid component 41 is extracted from a center portion of fluid channel 32.

By such a constitution, one node 70 is formed at inside of fluid channel 32. Thereby, there is realized small-sized component separating device 30 in which solid component 41 is agglomerated to node 70 at the center portion of fluid channel 32 and solid component 41 is easily taken out. In addition thereto, since component separating device 30 is driven by a low voltage, component separating device 30 realizes a method of separating the component for efficiently separating the component.

In addition thereto, actuator 39b is applied with a high frequency voltage which is provided with a frequency the same as that of the high frequency voltage applied to actuator 39a and a phase of which is inverted by 180 degrees. Thereby, an intensity of the standing wave formed at inside of fluid channel 32 is intensified. That is, there is formed the standing wave having the stronger intensity including one node 70 formed in parallel with fluid channel 32 at inside of fluid channel 32. The standing wave having the strong intensity achieves an effect of intensifying a force of agglomerating solid component 41 to node 70. Thereby, a separating function of separating solid component 41 from fluid 63 is promoted.

Actuator 39c is applied with a high frequency voltage having a frequency and a phase the same as those of the high frequency voltage applied to actuator 39a. At the same time, actuator 39d is applied with a high frequency voltage having a frequency and a phase the same as those of the high frequency voltage applied to actuator 39b. Thereby, a standing wave having a further stronger intensity is generated at inside of fluid channel 32. Similarly, the standing wave includes one node 70 in parallel with fluid channel 32 at inside of fluid channel 32. The standing wave having the further stronger intensity achieves an effect of further intensifying the force of agglomerating solid component 41 to node 70. Thereby, the separating function of separating solid component 41 from fluid 63 is further promoted.

As described above, by generating a standing wave having an odd number of nodes 70, solid component 41 is efficiently separated from fluid 63. Actuators 39a, 39b, 39c, 39d are applied with a high frequency voltage constituting the width W of fluid channel 32 by $\lambda/2$, or $n\lambda+\lambda/2$ (n designates a positive integer). Thereby, the standing wave having an odd number of nodes 70 is generated at inside of fluid channel 32.

As shown by FIG. 6, actuator 39a can also be applied with a high frequency voltage by which the width W of fluid channel 32 and the wavelength $\lambda$ of a supersonic wave becomes the same (W=$\lambda$). In this case, a standing wave generated at inside of fluid channel 32 includes two nodes 71 constituting an even number in parallel with fluid channel 32. When the standing wave having nodes 71 is formed, solid component 41 is agglomerated by constituting two rows and two rows of flows 43 are formed.

By such a constitution, as shown by FIG. 6, flow 42 is produced at the center portion of fluid channel 32 and flows 43 are produced at sides of wall faces 32a of fluid channel 32. After fluid 63 flows out from flow outlet 34, by branching flow 42 and flow 43, fluid 65 agglomerated with solid component 41 is extracted from the sides of wall faces 32a of fluid channel 32 and liquid component 64 is extracted from the center portion of fluid channel 32. That is, liquid component 64 is taken out efficiently from fluid 63.

Actuator 39a is applied with the high frequency voltage constituting the width W of fluid channel 32 by $n\lambda$ (n designates a positive integer). Thereby, a standing wave having an even number of nodes 71 in parallel with fluid channel 32 is generated at inside of fluid channel 32.

Actuator 39b is applied with a high frequency voltage having a frequency and a phase the same as those of the high frequency voltage applied to actuator 39a. Thereby, a sanding wave having the stronger intensity having two of nodes 71 at inside of fluid channel 32 is generated. The standing wave having the strong intensity achieves an effect of intensifying a force of agglomerating solid component 41 to nodes 71. Thereby, liquid component 64 is separated from fluid 63 further efficiently.

Next, an explanation will be given of a method of separating a component in which from a fluid including particles constituting a plurality of kinds of solid components having different sizes, the respective solid components are separated in reference to FIG. 7 and FIG. 8.

A speed of agglomerating the solid component to the node of the standing wave differs by a property of a particle of the solid component, that is, a size of the particle. In other word, the larger the size of the particle, the larger the influence of a pressure received from the standing wave. Thereby, a large particle is agglomerated to nodes 70, 71 faster than a small particle. By utilizing such a property, separation of the solid component in accordance with the size of the particle can be carried out.

For example, inside of fluid channel 32 is formed with first region 72 (hereinafter, referred to as region 72) at which a standing wave having an odd number pieces of nodes 70 is generated and second region 73 (hereinafter, referred to as region 73) at which a standing wave having an even number pieces of nodes 71 is generated. Thereby, separation of the liquid component and the solid component, or separation of solid components having different properties is easily carried out. That is, when a fluid is shifted from region 72 at which a standing wave having node 70 is generated, to region 73 at which a standing wave having node 71 is generated, there is utilized a difference of a speed of agglomerating two kinds or more of solid components having different properties to nodes 70, 71. A detailed explanation will be given of a method of separating a component utilizing the difference of the speed of agglomerating to nodes 70, 71 in reference to FIG. 7 and FIG. 8 as follows.

Figure 7:
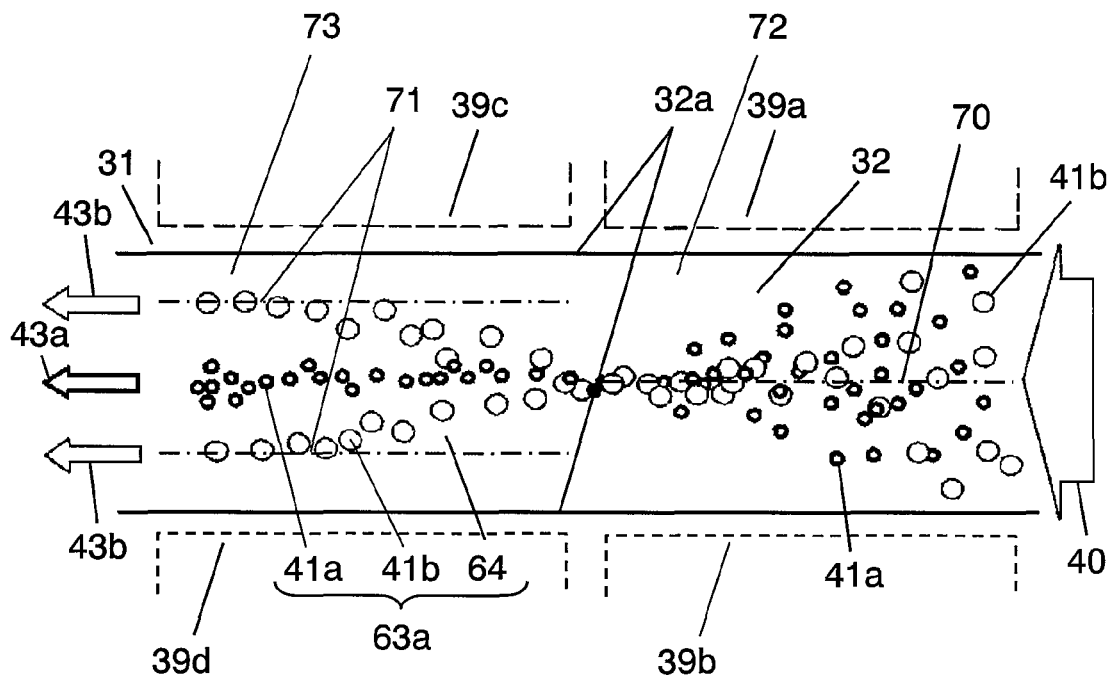
FIG. 7 is a schematic view for explaining the method of separating the component using the component separating device shown in FIG. 1.

First, as shown by FIG. 7, fluid 63 is inputted to fluid channel 32 from flow inlet 33. Fluid 63 is a mixture fluid mixed with solid component 41 and liquid component 64. Solid component 41 includes first solid component 41a (hereinafter, referred as solid component 41a) and second solid component 41b (hereinafter, referred to as solid component 41b) respectively having different sizes. A particle size of solid component 41a is smaller than that of solid component 41b. Normally, when component separating device 30 is not operated, fluid 63 flows at inside of fluid channel 32 in a state of irregularly mixing together solid components 41a, 41b and fluid component 64.

When component separating device 30 is operated, actuator 39a and actuator 39c are respectively applied with high frequency voltages. When actuators 39a, 39c are applied with high frequency voltages, supersonic vibrations are respectively generated.

A frequency of the high frequency voltage applied to actuator 39a is a frequency of a supersonic wave band constituting the width W of fluid channel 32 by ½ of the wavelength λ (λ=2×W). The supersonic wave vibration generated from the actuator 39a is transmitted at substrate 31 to generate a standing wave at inside of fluid channel 32. The standing wave generated by actuator 39a includes one node 70 constituting an odd number in parallel with fluid channel 32. Fluid 63 contained at inside of fluid channel 32 is made to flow at inside of fluid channel 32 such that solid components 41a, 41b are agglomerated to node 70.

A frequency of the high frequency voltage applied to actuator 39c is a frequency of a supersonic wave band constituting the width W of fluid channel 32 the same as that of the wavelength λ (λ=W). The supersonic vibration generated from actuator 39c is transmitted at substrate 31 to generate a standing wave at inside of fluid channel 32. The standing wave generated by actuator 39c includes two of nodes 71 of an odd number in parallel with fluid channel 32.

At this occasion, the high frequency voltage applied to actuator 39c is controlled to generate a standing wave having an intensity to a degree by which solid component 41b is agglomerated to node 71 and solid component 41a is difficult to be effected with an influence of the standing wave and is not agglomerated to node 71. Thereby, as shown by FIG. 7, solid component flow 43b (hereinafter, referred to as flow 43b) agglomerated with solid component 41b is produced on the sides of wall faces 32a of fluid channel 32 and solid component flow 43a (hereinafter, referred to as flow 43a) agglomerated with solid component 41a is produced at a center portion of fluid channel 32. Therefrom, solid component 41a and solid component 41b respectively having different sizes are efficiently separated.

Next, an explanation will be given of other method of separating solid component 41a and solid component 41b having different sizes in reference to FIG. 8.

Figure 8:
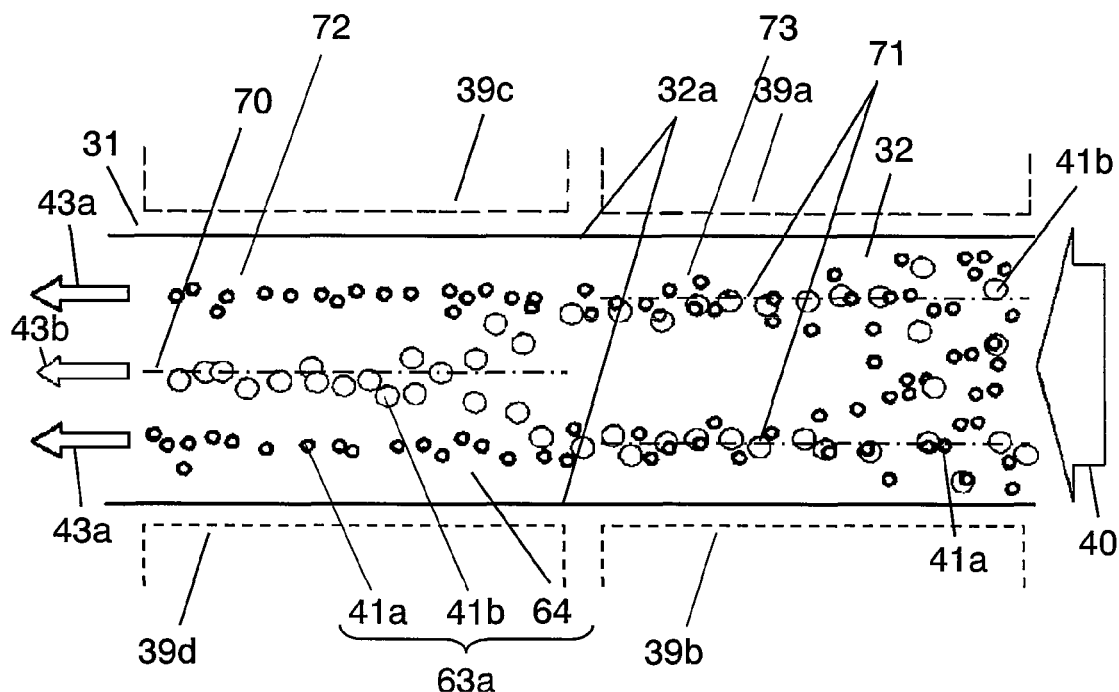
FIG. 8 is a schematic view for explaining the method of separating the component using the component separating device shown in FIG. 1.

As shown by FIG. 8, high frequency voltages are applied respectively to actuator 39a and actuator 39c. When actuators 39a, 39c are applied with high frequency voltages, supersonic wave vibrations are respectively generated.

A frequency of the high frequency voltage applied to actuator 39a is a frequency of supersonic band constituting the width W of fluid channel 32 the same as the wavelength λ (λ=W). By applying the high frequency voltage to actuator 39a, actuator 39a generates a standing wave having two of an even number of nodes 71 in parallel with fluid channel 32 at inside of fluid channel 32. Fluid 63 contained at inside of fluid channel 32 is made to flow at inside of fluid channel 32 such that solid components 41a, 41b are agglomerated to nodes 71.

A frequency of the high frequency voltage applied to actuator 39c is a frequency of a supersonic wave band constituting the width W of fluid channel 32 by ½ of a wavelength λ (λ=2×W). By applying the high frequency voltage to actuator 39c, actuator 39c generates a standing wave having constituting an odd number of one node 70 in parallel with fluid channel 32 at inside of fluid channel 32.

At this occasion, the high frequency voltage applied to actuator 39c is controlled to generate a standing wave having an intensity to a degree by which solid component 41b is agglomerated to node 70 and solid component 41a is difficult to be effected with an influence of the standing wave and is not agglomerated to node 70. Thereby, as shown by FIG. 8, flow 43a agglomerated with solid component 41a is produced on the sides of wall faces 32a of fluid channel 32 and flow 43b agglomerated with solid component 41b is produced at the center portion of fluid channel 32. Therefrom, solid component 41a and solid component 41b respectively having different sizes are efficiently separated.

By the constitution explained above, from fluid 63 including two kinds or more of solid components 41a, 41b having different properties, by utilizing the difference of the speeds of agglomerating the solid components 41a, 41b to nodes 70, 71, respective solid components 41a, 41b are separated.

An explanation about driving actuators 39b, 39d is omitted. However, in order to increase intensities of the standing waves generated by actuators 39a, 39c respectively opposed to each other by way of fluid channel 32, predetermined high frequency voltage may be applied to actuators 39b, 39d.

Solid component 41a and solid component 41b respectively having different sizes may be separated not only by a combination of actuator 39a and actuator 39c but also a combination of actuator 39a and actuator 39d.

An explanation has been given of separation in accordance with the size of the particle with regard to separation of solid component 41a and solid component 41b respectively having different properties. However, when not only the size of the particle differs but also, for example, a property of a specific weight, shape, surface energy or the like of the solid component differs, the above-described method of separating the component is applicable. As mentioned above, component separating device 30 realizes the efficient method of separating the component.

Next, a method of fabricating component separating device 30 will be explained in reference to FIG. 9 through FIG. 14. FIG. 9 through FIG. 14 are sectional views showing a procedure of fabricating the component separating device according to Embodiment 1.

Figure 9:
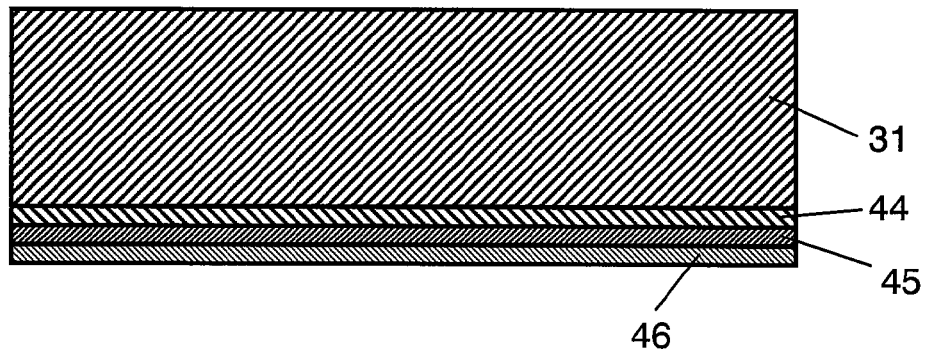
FIG. 9 is a sectional view for explaining a method of fabricating the component separating device shown in FIG. 1.

First, as shown by FIG. 9, first electrode layer 44 (hereinafter, referred to as electrode layer 44), piezoelectric 45 and second electrode layer 46 (hereinafter, referred to as electrode layer 46) are formed successively above substrate 31 made from silicon. Electrode layer 44 includes at least either one of titanium and platinum. Piezoelectric layer 45 includes lead zirconate titanate. Electrode layer 46 includes at least either one of titanium and gold. Electrode layer 44, piezoelectric layer 45 and electrode layer 46 are formed by a thin film forming technology. A thin film forming method used in forming electrode layers 44, 45 is a generally used thin film forming method of sputtering, vapor deposition or the like.

As a thin film forming method used in forming piezoelectric layer 45, a sputtering method, a hydrothermal synthesis method, sol gel process or the like is applicable. Particularly, a piezoelectric thin film having a high piezoelectric property and achieving a stable displacement is provided for piezoelectric layer 45 formed by a sputtering method by using a material of lead zirconate titanate or the like.

Figure 10:
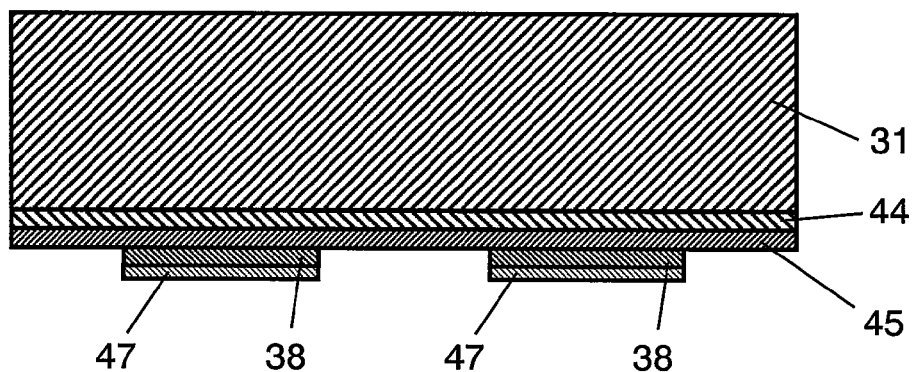
FIG. 10 is a sectional view for explaining the method of fabricating the component separating device shown in FIG. 1.

Next, first resist mask 46 (hereinafter, referred to as mask 47) having a predetermined pattern is formed on electrode layer 46 which is a top layer. As shown by FIG. 10, electrode layer 46 is patterned by an etching by constituting mask 47 as a mask for the etching. Thereby, upper electrode 38 is formed. Thereafter, mask 47 is removed by an etching method or the like.

Figure 11:
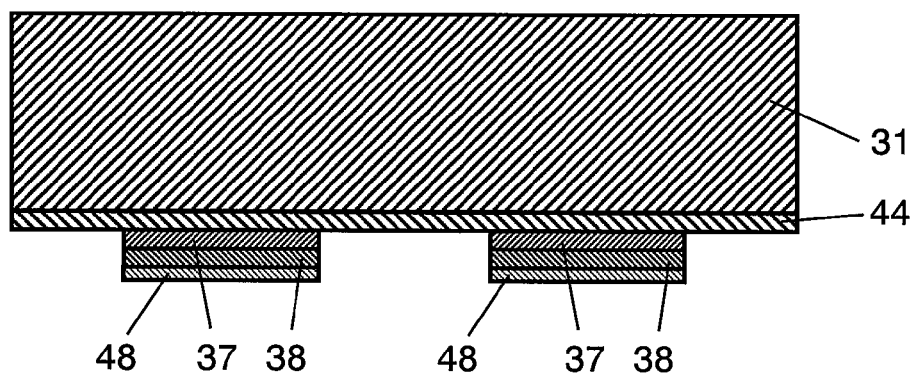
FIG. 11 is a sectional view for explaining the method of fabricating the component separating device shown in FIG. 1.

Next, second resist mask 48 (hereinafter, referred to as mask 48) having a predetermined pattern is formed on upper electrode 38. By constituting mask 48 as a mask for an etching, as shown by FIG. 11, piezoelectric layer 45 is patterned by the etching to be divided similarly. Thereby, piezoelectric member 37 is formed. Thereafter, mask 48 is removed by an etching method or the like.

Figure 12:
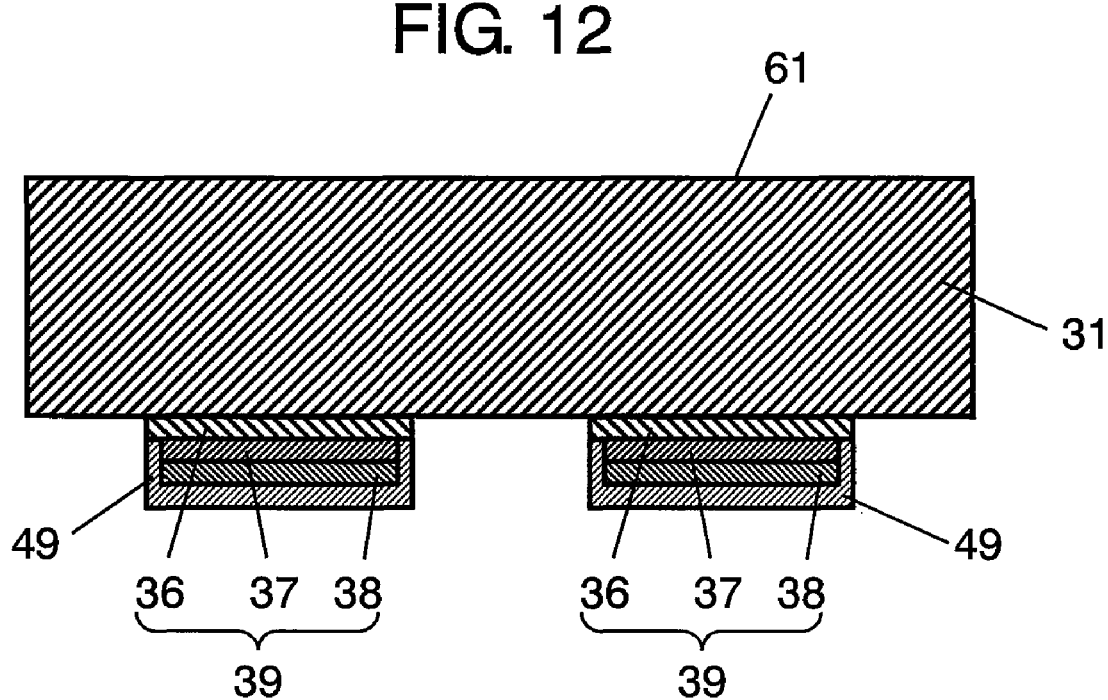
FIG. 12 is a sectional view for explaining the method of fabricating the component separating device shown in FIG. 1.

Next, third resist mask 49 (hereinafter, referred to as mask 49) having a predetermined pattern is formed to cover upper electrode 38 and piezoelectric member 37. By constituting mask 49 as a mask for an etching, as shown by FIG. 12, electrode layer 44 is patterned by the etching. Thereby, lower electrode 36 is formed. Thereafter, mask 49 is removed by an etching method or the like.

Figure 13:
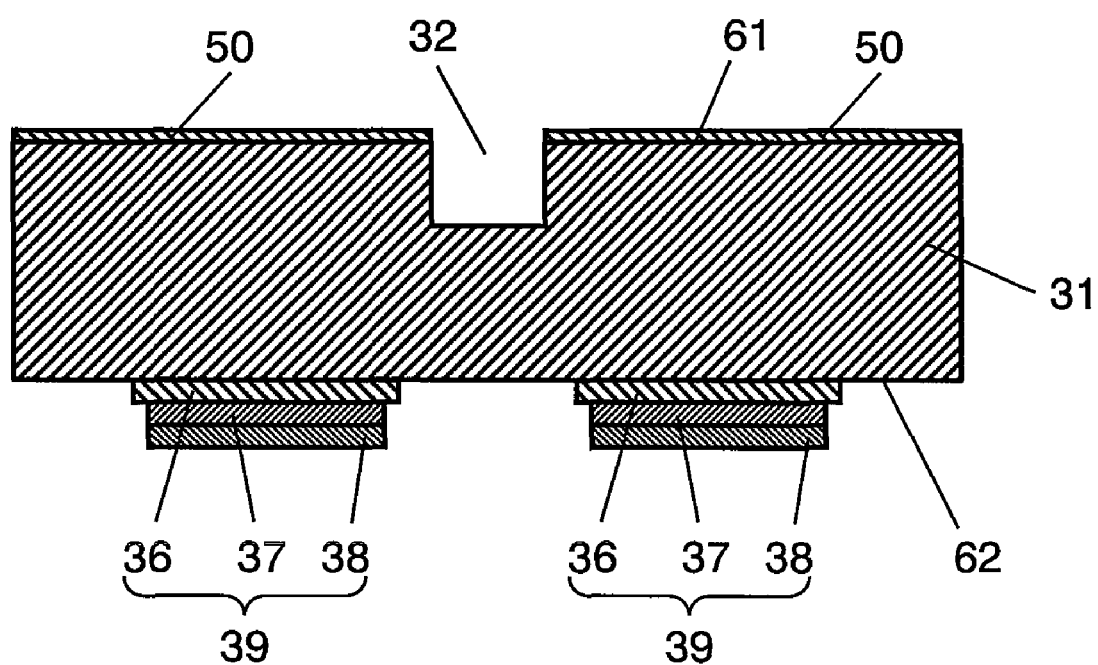
FIG. 13 is a sectional view for explaining the method of fabricating the component separating device shown in FIG. 1.

Next, upper face 61 is formed with fourth resist mask 50 (hereinafter, referred to as mask 50) having a predetermined pattern. By constituting mask 50 as a mask for an etching, as shown by FIG. 13, substrate 31 is patterned by the etching. Thereby, fluid channel 32 is formed. Thereafter, mask 50 is removed by an etching method or the like.

Figure 14:
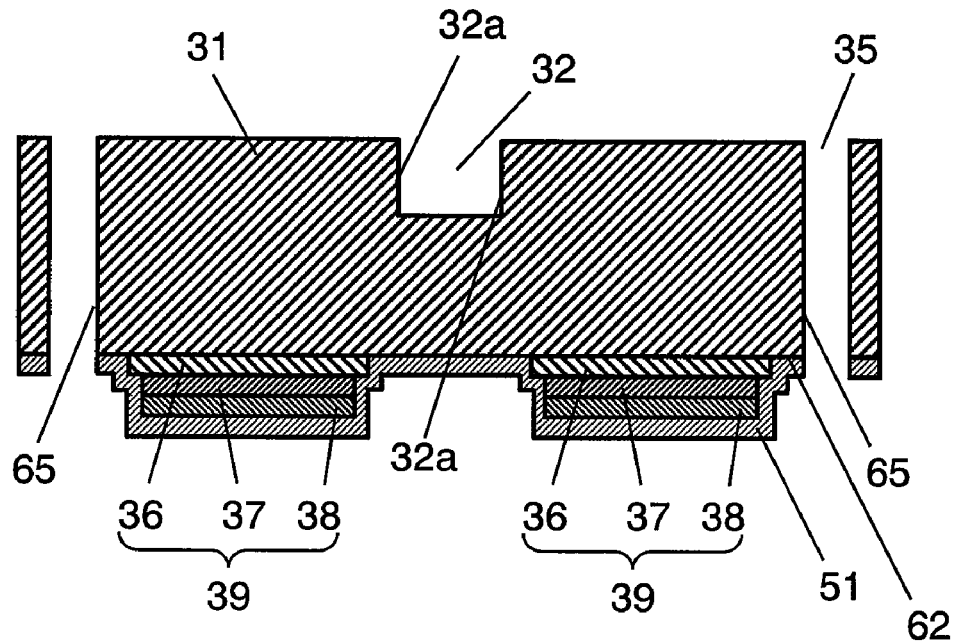
FIG. 14 is a sectional view for explaining the method of fabricating the component separating device shown in FIG. 1.

Next, lower face 62 is formed with fifth resist mask 51 (hereinafter, referred to as mask 51) having a predetermined pattern. By constituting mask 51 as a mask for an etching, as shown by FIG. 14, substrate 31 is etched. Thereby, groove 35 is formed at substrate 31. At this occasion, the deeper the depth of groove 35, the smaller the leakage of vibration, and vibration is reflected efficiently. Therefore, it is preferable that groove 35 is a through hole. After forming groove 35, mask 51 is removed by an etching method or the like.

At steps shown by FIG. 13 and FIG. 14, a dry etching method is used as the method of etching substrate 31. Thereby, fluid channel 32 and groove 35 having fine shapes are machined to be formed highly accurately. In machining by the dry etching method, the dry etching is carried out by mixing a gas for promoting etching and a gas for inhibiting etching. Thereby, fluid channel 32 and groove 35 are machined further highly accurately.

Component separating device 30 is fabricated by the above-described fabricating method.

Figure 15:
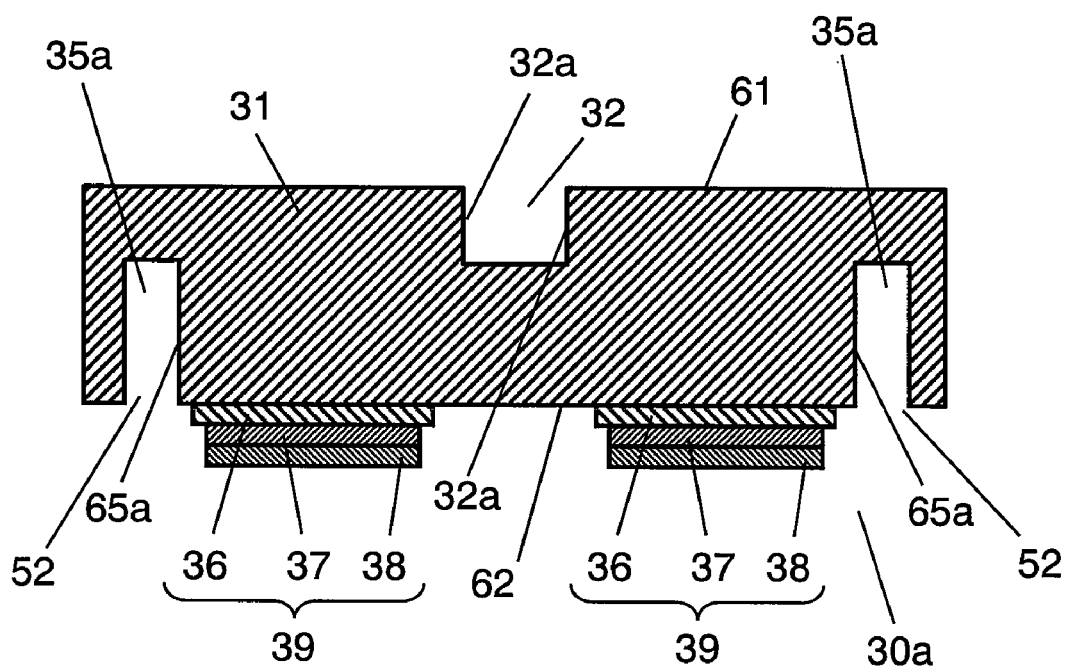
FIG. 15 is a sectional view for showing a constitution of a component separating device according to other configuration.

According to component separating device 30 having the above-described constitution, groove 35 is provided with a shape of a through hole. Groove 35 includes first opening portion 52 (hereinafter, referred to as opening portion 52) on a side of lower face 62 and second opening portion 53 (hereinafter, referred to as opening portion 53) on a side of upper face 61. However, groove 35 is not necessarily limited to a through hole. For example, as shown by FIG. 15, groove 35a may be constituted by a shape of a hole having opening portion 52 opened only on the side of lower face 62 and having a bottom portion which is not opened to the side of upper face 61.

Even when groove 35a having a hole shape, a vibration generated by actuators 39 is reflected by wall face 65a of groove 35a and a reflected wave is transmitted to fluid channel 32. Since the opening portion is not provided on the side of upper face 61, fluid 63 can be prevented from being leaked out by way of groove 35a. Component separating device 30a having a high mechanical strength is realized.

Second Exemplary Embodiment

An explanation will be given of a component separating device according to Embodiment 2 of the invention in reference to the drawings as follows.

Figure 16:
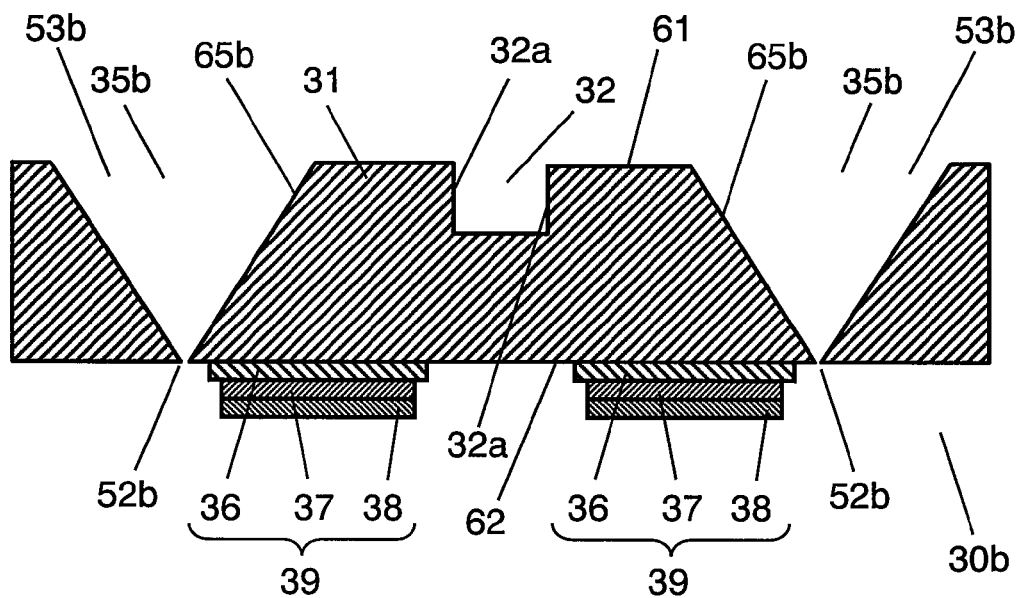
FIG. 16 is a sectional view showing a constitution of a component separating device according to Embodiment 2 of the invention.

FIG. 16 is a sectional view showing a configuration of the component separating device according to Embodiment 2 of the invention. A point by which Embodiment 2 differs from Embodiment 1 resides in a sectional shape of a groove. Groove 35b according to Embodiment 2 includes first opening portion 52b (hereinafter, referred to as opening portion 52b) on the side of lower face 62 and second opening portion 53b (hereinafter, referred to as opening portion 53b) on the side of upper face 61. Further, opening portion 52b is smaller than opening portion 53b. Thereby, an angle made by wall face 65b, which is a wall face provided at a side of the fluid channel of groove 35b, and lower face 62 provided with actuators 39 is an acute angle.

The vibration generated by actuator 39 includes a vibration component directly transmitted to fluid channel 32 and reflected wave reflected by wall face 65b of groove 35b to be transmitted to fluid channel 32. By making opening portion 52b smaller than opening portion 53b, wall face 65b is provided with an inclination, and a distance by which the reflected wave reaches fluid channel 32 is shortened. Thereby, vibration is efficiently transmitted from actuators 39 to fluid channel 32. As a result, the intensity of the standing wave at inside of fluid channel 32 is increased.

By such a constitution, the vibration generated by actuators 39 can utilize the reflected wave having the short distance of reaching fluid channel 32. In addition thereto, an angle of incidence by which the standing wave transmitted to fluid channel 32 is incident on wall face 32a of fluid channel 32 is constituted by a further acute angle. Therefore, component separating device 30b capable of separating the component further efficiently is realized.

Groove 35b is formed as a through hole having opening portions 52b, 53b having different sizes by a wet etching method. For example, substrate 31 having inclined wall face 65b is fabricated by executing etching while utilizing crystal anisotropy of substrate 31.

Third Exemplary Embodiment

An explanation will be given of a component separating device according to Embodiment 3 of the invention in reference to the drawings as follows.

Figure 17:
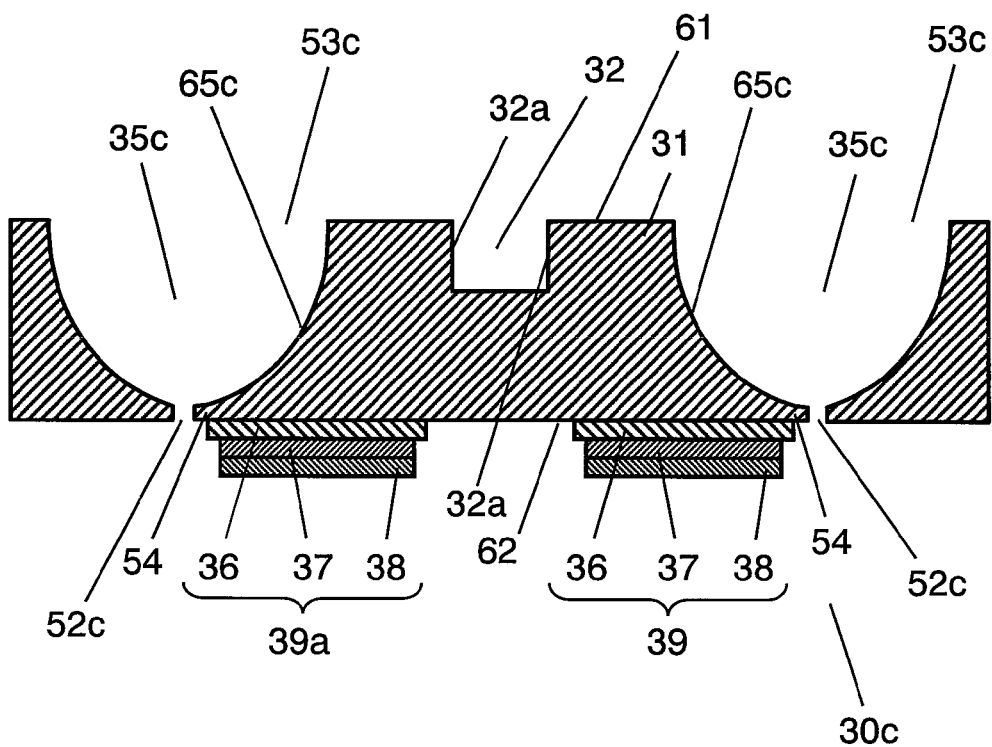
FIG. 17 is a sectional view showing a constitution of a component separating device according to Embodiment 3 of the invention.

FIG. 17 is a sectional view showing a configuration of the component separating device according to Embodiment 3 of the invention. A point by which Embodiment 3 differs from Embodiments 1 or 2 resides in a sectional shape of a groove. A groove 35c according to Embodiment 3 includes first opening portion 52c (hereinafter, referred to as opening portion 52c) on the side of lower face 62 and second opening portion 53c (hereinafter, referred to as opening portion 53c) on the side of upper face 61. Opening portion 52c and opening portion 53c are connected by wall face 65c. A sectional shape of wall face 65c is constituted by a circular arc or an elliptical curve having a center at a side of groove 35c.

By such a constitution, the vibration generated by actuators 39 is reflected by wall face 65c and the distance of reaching fluid channel 32 is further shortened. Thereby, a further stronger reflected wave can be utilized.

Actuators 39 are provided at movable portion 54 of substrate 31. By constituting a sectional shape of wall face 65c by a circular arc or an elliptical curve, a thickness of movable portion 24 is thin. Therefore, the vibration generated by actuators 39 is easy to be transmitted to fluid channel 32, and a standing wave having a further larger intensity is provided.

Groove 35c having such a shape can be formed by an isotropic dry etching using, for example, $XeF_2$, $SF_6$ gas or the like. That is, substrate 31 is etched from a side of opening portion 53c by the isotropic dry etching method, and a shape of groove 35c is easily provided.

INDUSTRIAL APPLICABILITY

The invention can easily separate respective components from a fluid mixed with a liquid component and a solid component represented by, for example, blood, milky liquid or the like and is used for a component separator, a component analyzer or the like.

The invention claimed is:

1. A component separating device comprising:
a substrate;
a fluid channel provided at the substrate for containing a fluid including a liquid component and a solid component;
an actuator for generating a standing wave at inside of the fluid channel; and
a groove provided at a surrounding of the actuator,
wherein the actuator is provided on the substrate.

2. The component separating device of claim 1,
wherein the groove is a through hole.

3. The component separating device of claim 1,
wherein the fluid channel and the actuator are provided in the same axial direction.

4. The component separating device of claim 1,
wherein a plurality of the actuators are arranged to be opposed to each other across the fluid channel.

5. The component separating device of claim 1,
wherein a plurality of the actuators are arranged along the fluid channel.

6. The component separating device of claim 1,
wherein the fluid channel is provided at an upper face of the substrate, and the actuator is provided at a lower face of the substrate.

7. The component separating device of claim 2,
wherein the groove includes
a first opening portion opened to a side of forming the actuator and
a second opening portion opened to a side opposed to the first opening portion, and
the first opening portion is smaller than the second opening portion.

8. The component separating device of claim 7,
wherein the groove includes
a wall face connecting the first opening portion and the second opening portion, and
a sectional shape of the wall face is constituted by at least either one of a circular arc and an elliptical curve having centers thereof on a side of the groove.

9. The component separating device of claim 1,
wherein the actuator is provided at a lower face of the substrate and
an angle made by a wall face of the groove on a side of the fluid channel and the lower face is an acute angle.

10. The component separating device of claim 1,
wherein a material of the substrate is silicon.

11. The component separating device of claim 1,
wherein the actuator includes a lower electrode and a piezoelectric member and an upper electrode,
a material of the lower electrode includes at least either one of titanium and platinum,
a material of the piezoelectric member includes lead zirconate titanate, and
a material of the upper electrode includes at least either one of titanium and gold.

12. A method of separating a component comprising:
a fluid containing step of containing a fluid including a liquid component and a solid component in a fluid channel provided at a substrate;
a standing wave generating step of generating a standing wave having a node at an inner portion of the fluid channel by generating a vibration by applying a high frequency voltage to a plurality of actuators provided to be opposed to the fluid channel;
a reflecting step of reflecting the vibration by a groove provided at a surrounding of the actuator, and the groove is removed at the surrounding of a side of the fluid channel; and
a separating step of separating at least either one of the liquid component and the solid component from the fluid.

13. The method of separating a component of claim 12,
wherein the standing wave generating step is a standing wave generating step of generating a standing wave having an odd number pieces of nodes at the fluid channel by generating a vibration by applying high frequency voltages respective phases of which differ from each other by 180 degrees to a first actuator and a second actuator respectively provided on both sides of the fluid channel to be opposed to each other.

14. The method of separating a component of claim 12,
wherein the standing wave generating step is a standing wave generating step of generating a standing wave having an even number pieces of nodes at the fluid channel by generating a vibration by applying high frequency voltages respective phases of which are the same to a first actuator and a second actuator provided respectively on both sides of the fluid channel to be opposed to each other.

15. The method of separating a component of claim 12,
wherein the standing wave generating step is a standing wave generating step of generating a standing wave having an odd number pieces of nodes and a standing wave having an even number pieces of nodes at the fluid channel by generating vibrations by applying high frequency voltages having frequencies respectively different from each other to a first actuator and a third actuator respectively provided along the fluid channel.

* * * * *